United States Patent
Karinka et al.

(10) Patent No.: US 6,801,041 B2
(45) Date of Patent: Oct. 5, 2004

(54) SENSOR HAVING ELECTRODE FOR DETERMINING THE RATE OF FLOW OF A FLUID

(75) Inventors: Shridhara Alva Karinka, Lowell, MA (US); Isabella Moser, Eichstetten (DE); Gerhard Jobst, Eichstetten (DE); Uwe Tietjen, Freiburg (DE); Panagiota S. Petrou, Kapandriti (GR); Uwe Herberth, Kirchzarten (DE); Gerald Urban, Freiburg (DE)

(73) Assignee: Abbott Laboratories, Abbott Park, IL (US)

( * ) Notice: Subject to any disclaimer, the term of this patent is extended or adjusted under 35 U.S.C. 154(b) by 65 days.

(21) Appl. No.: 10/145,837

(22) Filed: May 14, 2002

(65) Prior Publication Data

US 2003/0214304 A1 Nov. 20, 2003

(51) Int. Cl.[7] .............................. G01N 27/02; G01F 1/56
(52) U.S. Cl. ...................... 324/444; 324/71.1; 600/347; 73/861.08; 73/170.01
(58) Field of Search ......................... 324/71.1, 92, 444; 73/170.01, 861, 861.08, 861.12, 170.08; 600/347

(56) References Cited

U.S. PATENT DOCUMENTS

| | | | |
|---|---|---|---|
| 4,953,552 A | * | 9/1990 | DeMarzo |
| 4,960,467 A | * | 10/1990 | Peck |
| 5,243,982 A | * | 9/1993 | Möstl et al. |

(List continued on next page.)

FOREIGN PATENT DOCUMENTS

| | | |
|---|---|---|
| DE | 196 53 436 | 12/1996 |
| EP | 0 946 867 B1 | 12/1997 |
| GB | 2 100 864 | 1/1983 |

OTHER PUBLICATIONS

Copy of The PCT Search Report US 03/15137.

*Primary Examiner*—N. Le
*Assistant Examiner*—Timothy J. Dole
(74) *Attorney, Agent, or Firm*—David L. Weinstein (57) ABSTRACT

Sensors that are capable measuring the rate of flow of a fluid that passes over the electrodes of the sensor. In these sensors, an electrode, designated the flow rate-determining electrode, is used in conjunction with the conventional electrodes, e.g., the working electrode, the reference electrode, and the counter electrode, to determine the rate of flow of the fluid. In one aspect, this invention provides a sensor for measuring the concentration of an analyte in a sample of fluid when the sample flows continuously over the electrodes of the sensor, especially when the rate of flow of the sample is relatively low. In another aspect, this invention provides a method for measuring the concentration of an analyte in a sample of fluid, wherein the rate of flow of the sample varies during the period of time that the sensor is in place. In a preferred embodiment, the sensor employs four electrodes, namely, a working electrode, a reference electrode, a counter electrode, and a flow rate-determining electrode. Alternatively, a single electrode that performs both the function of the reference electrode and the function of the counter electrode can replace the reference electrode and the counter electrode. In addition, a dummy electrode or a blank electrode can be used to compensate for interference from electrochemically active species. The reagent(s) specific to the analyte of interest is required to be deposited on the working electrode.

48 Claims, 5 Drawing Sheets

U.S. PATENT DOCUMENTS

| | | | |
|---|---|---|---|
| 5,291,887 A | * | 3/1994 | Stanley et al. |
| 5,362,307 A | * | 11/1994 | Guy et al. |
| 5,469,846 A | * | 11/1995 | Khan |
| 5,507,288 A | * | 4/1996 | Böcker et al. |
| 5,527,288 A | * | 6/1996 | Gross et al. |
| 5,582,184 A | * | 12/1996 | Erickson et al. |
| 5,636,632 A | * | 6/1997 | Bommannan et al. |
| 5,640,954 A | * | 6/1997 | Pfeiffer et al. |
| 5,820,570 A | * | 10/1998 | Erickson et al. |
| 5,885,211 A | * | 3/1999 | Eppstein et al. |
| 5,951,493 A | * | 9/1999 | Douglas et al. |
| 6,013,029 A | | 1/2000 | Korf et al. .......... 600/363 |
| 6,134,461 A | * | 10/2000 | Say et al. |
| 6,214,206 B1 | * | 4/2001 | Kriz |

* cited by examiner

SENSOR HAVING ELECTRODE FOR DETERMINING THE RATE OF FLOW OF A FLUID

BACKGROUND OF INVENTION

1. Field of the Invention

This invention relates to sensors that are capable of determining the rate of flow of a fluid. More particularly, the sensors can be used to determine the concentration of an analyte in a sample of fluid in a continuous manner where the rate of flow of the sample of fluid is expected to vary during the determination.

2. Discussion of the Art

Determination of the rate of flow of a fluid is important in systems designed for chemical analysis of samples of fluid and delivery of chemicals such as drugs. When the rate of flow of a fluid is known, one can accurately determine the concentration of an analyte in the fluid, even if it is a slow-moving fluid, or the concentration of a chemical in a formulation being delivered from a reservoir.

Certain sensors, known as continuous monitoring biosensors, can be used to continuously monitor the concentration of an analyte in a biological sample under either in vivo or in vitro conditions. For example, the concentration of glucose in a body fluid can be monitored continuously so that the patient will have a better understanding of variations in concentration of glucose in the blood, and, consequently will be able to modify his diet or medications. In general, the concentration of glucose in the blood is expected to change significantly during normal activity, such as consuming a meal, exercising, etc. Biosensors that have been disclosed for this function are described in U.S. Pat. Nos. 4,953,552; 4,960,467; 5,243,982; 5,291,887; 5,362,307; 5,469,846; 5,507,288; 5,527,288; 5,636,632; 6,134,461, all of which are incorporated herein by reference. Methods and devices for extracting the biological sample from the body are described in U.S. Pat. Nos. 5,582,184; 5,820,570, 5,951,493; 5,885,211, 5,640,954, all of which are incorporated herein by reference.

Continuous monitoring biosensors are also used in pharmaceutical or industrial applications to monitor analytes in flow injection analysis (FIA) systems. In these applications, a pump, such as an automated syringe pump, can accurately control the rate of flow of the sample through the biosensor. Biosensors that have been disclosed for this function are described in U.S. Pat. No. 6,214,206, incorporated herein by reference. Biosensors that are suitable for use in applications involving continuous monitoring typically rely on either detection of at least one reaction product, such as hydrogen peroxide, or detection of electric current with the aid of a mediator. Such biosensors typically include two or three electrodes. A biosensor having three electrodes has a working electrode, a reference electrode, and a counter electrode. A biosensor having two electrodes has a working electrode and a dual-purpose electrode, which functions as both a reference electrode and a counter electrode.

When a biological sample is continuously drawn out of the body of a patient for continuous measurement of the concentration of an analyte, such as, for example, glucose, the rate of flow of the sample may vary on account of one or more reasons. For example, when the biological sample is interstitial fluid, the rate of excretion of interstitial fluid from the body can vary depending on the level of vacuum aiding in removal of the sample from the body of the patient or the hydration state of the patient. The level of vacuum can vary on account of a leak in the vacuum. When the patient is overhydrated, the rate of flow of interstitial fluid can be relatively high; when the patient is dehydrated, the rate of flow of interstitial fluid can be relatively low. Furthermore, healing or inflammation at the site of the body at which the interstitial fluid is collected during the course of operation of the biosensor can also result in variations in the rate of flow. Because the rate of diffusion of the analyte to the surface of the working electrode of the biosensor is dependent on rate of flow of the fluid emerging from the body, the response of the biosensor will be dependent upon the rate of flow of the fluid. Situations involving continuous removal of the biological sample from the body for continuous measurement of an analyte can be contrasted with situations where the biosensor is implanted in the body of a patient, wherein it is presumed that there are no variations in the rate of flow, because the biosensor is immersed in a pool of the sample. In pharmaceutical or industrial applications, the rate of flow is controlled externally, typically by means of a peristaltic pump or a motorized syringe pump.

In order to measure the rate of flow of a biological fluid as it is being drawn out of the body of a patient, an additional device can be used for the measurement of rate of flow of the sample. This additional device would have to be placed in the flow path of the sample, thereby causing an increase in the dimensions of the flow path, and hence, an increase the in the volume of sample required. Moreover, an additional measurement system would be required, whereby the cost of the biosensor system would be increased.

Other means for testing the rate of flow of fluid involve the introduction of air bubbles (i.e., an air plug) to the flow path. The introduction of air bubbles allows one to monitor the movement of the air-liquid interface. There are methods and devices available for the detection of air-liquid interface by thermal or spectroscopic methods, whereby the rate of flow of the fluid can be determined by determining the rate of flow of the air bubbles or the air-liquid interface.

A biosensor for continuously monitoring the concentration of an analyte, such as, for example, glucose, can be constructed by immobilizing an enzyme, such as, for example, glucose oxidase, on the surface of the working electrode of the biosensor. The analyte in the biological sample is oxidized at the working electrode and the electrochemically active reaction product, such as, for example, hydrogen peroxide, can diffuse to the surface of the working electrode and to the channel of the biosensor through which the biological sample is flowing, i.e., the flow channel. A portion of this electrochemically active reaction product can diffuse back to the working electrode from the flow channel, thereby affecting the response of the biosensor. At low rates of flow of biological samples, the extent of back diffusion is significantly higher than that at high rates of flow. As a result, the response of the biosensor, e.g., the current measured, is dependent upon the rate of flow of the sample, with the response being higher at lower rates of flow. For biosensors for continuous monitoring of biological fluid, particularly when the sample is drawn out of the body from an artificial opening in the skin, the rate of flow of the sample becomes extremely important.

Accordingly, it would be desirable to develop a biosensor for continuously monitoring a biological sample, without the need for any additional devices or additional steps to measure the rate of flow of the sample.

SUMMARY OF THE INVENTION

In one aspect, this invention provides various types of sensors that are capable of measuring the rate of flow of a fluid that passes over the electrodes of the sensor. In any of these sensors, an electrode, designated the flow rate-determining electrode, is used in conjunction with the conventional electrodes, e.g., the working electrode, the reference electrode, and the counter electrode, to determine the rate of flow of the fluid.

In another aspect, this invention provides a sensor for measuring the concentration of an analyte in a sample of fluid when the sample flows continuously over the electrodes of the sensor, especially when the rate of flow of the biological sample is relatively low. In another aspect, this invention provides a method for measuring the concentration of an analyte in a sample of fluid, wherein the rate of flow of the sample varies during the period of time that the sensor is in place. Sensors that are used for measuring one or more parameters of a biological sample, e.g., the concentration of an analyte, are referred to herein as biosensors.

In a preferred embodiment, the sensor employs four electrodes, namely, a working electrode, a reference electrode, a counter electrode, and a flow rate-determining electrode. Alternatively, a single electrode that performs both the function of the reference electrode and the function of the counter electrode can replace the reference electrode and the counter electrode. In addition, a dummy electrode or a blank electrode can be used to compensate for interference from electrochemically active species. The reagent(s) specific to the analyte of interest is (are) required to be deposited on the working electrode.

In addition to the electrodes normally contained in a sensor, e.g., the working electrode, the reference electrode, the counter electrode, the sensor comprises a flow rate-determining electrode, which measures the quantity of electrochemically active species that diffuses to the flow path of the fluid that flows in the flow channel of the sensor. A calibration relationship can be established for relating the rate of flow of the fluid and the response of the flow rate-determining electrode or for relating the rate of flow of the fluid and the ratio of the responses of the flow rate-determining electrode and the working electrode.

In one embodiment, the rate of flow of a sample of fluid can be determined from the response of the working electrode and the response of the flow rate-determining electrode. In a second embodiment, the rate of flow of a sample of fluid can be determined from the response of a working electrode that has been modified to render it insensitive to changes in the rate of flow of the sample and the response of a flow rate-determining electrode that has been designed to render it sensitive to changes in the rate of flow of the sample. In a third embodiment, the rate of flow of a sample of fluid can be determined from the response of the working electrode and the response of the flow rate-determining electrode along with the knowledge of the direction of flow of the sample.

The inclusion of the flow-rate determining electrode in the sensor enables the accurate determination of the concentration of the analyte regardless of the rate of flow of the sample. The flow rate-determining electrode is preferably fabricated at the same time as the other electrodes; no additional fabrication step is required.

DETAILED DESCRIPTION

Figure 4:
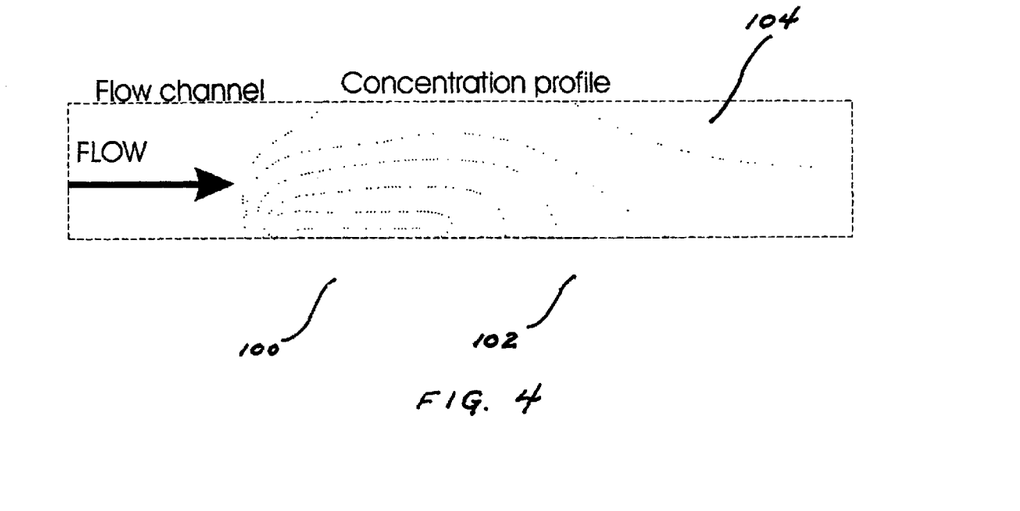
FIG. 4 is a schematic view showing the positioning of the working electrode and the flow rate-determining electrode in the flow channel of a sensor of this invention in which the sample contacts the working electrode prior to contacting the flow rate-determining electrode. In the embodiment shown in this schematic view, the working electrode is sensitive to changes in the rate of flow of the fluid, and the flow rate-determining electrode is also sensitive to changes in the rate of flow of the fluid.
Figure 5:
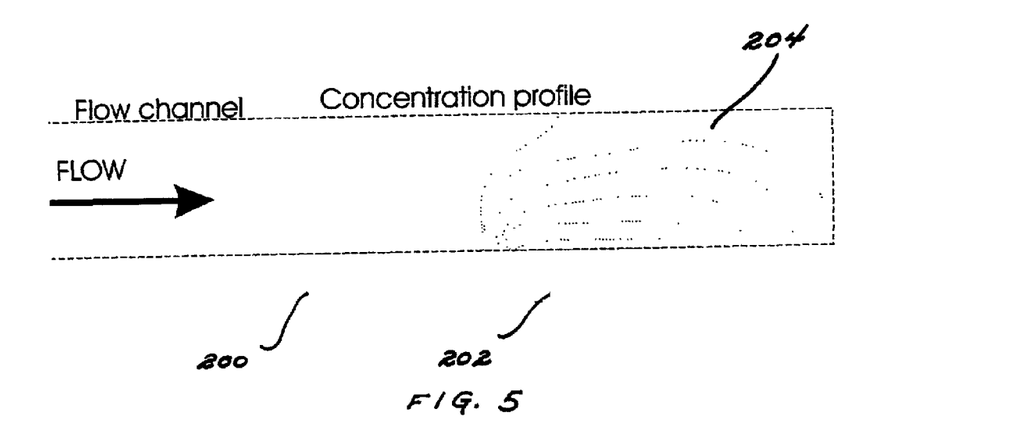
FIG. 5 is a schematic view showing the positioning of the working electrode and the flow rate-determining electrode in the flow channel of a sensor of this invention in which the sample contacts the working electrode prior to contacting the flow rate-determining electrode. In the embodiment shown in this schematic view, the working electrode is not sensitive to changes in the rate of flow of the fluid, and the flow rate-determining electrode is sensitive to changes in the rate of flow of the fluid.
Figure 6:
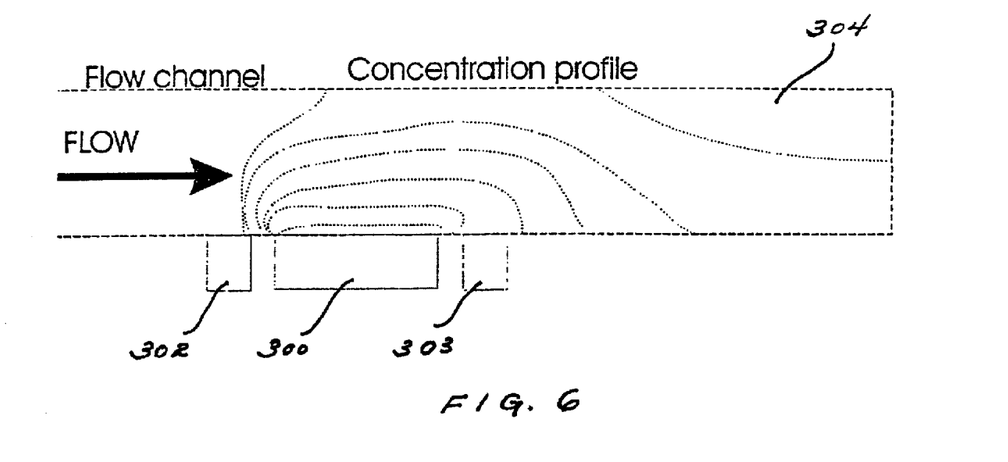
FIG. 6 is a schematic view showing positioning of the working electrode and two flow rate-determining electrodes in the flow channel of a sensor of this invention in which the sample contacts the working electrode prior to contacting the flow rate-determining electrode. In the embodiment shown in this schematic view, both the rate of flow of the fluid and the direction of flow of the fluid can be determined. In the embodiment shown in this schematic view, the working electrode is sensitive to changes in the rate of flow of the fluid, and the flow rate-determining electrodes are also sensitive to changes in the rate of flow of the fluid.

As used herein, the expression "flow rate-determining electrode" means the electrode that is used to determine the response that is dependent upon the rate of flow of the sample. The flow rate-determining electrode need not generate any electrochemically active species. The term "sensor" means a device that detects and responds to a signal or stimulus. The term "biosensor" means a sensor that can be used to determine one or more parameters of a biological sample, more particularly, trace and low levels of biologically active substances in a biological sample. The expression "flow channel" means the channel through which the sample of interest flows in the biosensor. The term "diffusion" means the process in which particles or molecules disperse, wherein particles or molecules move from a region in which the concentration of the particles or molecules is higher to a region in which the concentration of the particles or molecules is lower. The expression "back diffusion" means the diffusion of particles or molecules in a direction opposite to the direction of flow of the sample. The term "response" means the signal measured by the sensor. In a typical situation, the signal is an electrical signal, e.g., current, generated by a chemical reaction, e.g., oxidation-reduction. The term "sensitive" means that the response changes as a result of a change in a parameter, such as for example, the rate of flow of a fluid. The term "insensitive" means that the response does not change as a result of a change in a parameter, such as for example, the rate of flow of a fluid. The expression "reaction layer" means the layer containing the reagent that reacts with, e.g., oxidizes, the analyte of interest. In the case of glucose, the reaction layer can contain the enzyme glucose oxidase. The term "blank" means lacking an active ingredient, such as, for example, an enzyme. The expression "concentration profile" refers to the distribution of hydrogen peroxide at any given time. In FIGS. 4, 5, and 6, each line indicates a given concentration of hydrogen peroxide. The concentration from one line to another varies. The concentrations of hydrogen peroxide decrease at increasing distances from the electrode that generated the hydrogen peroxide.

Figure 1:
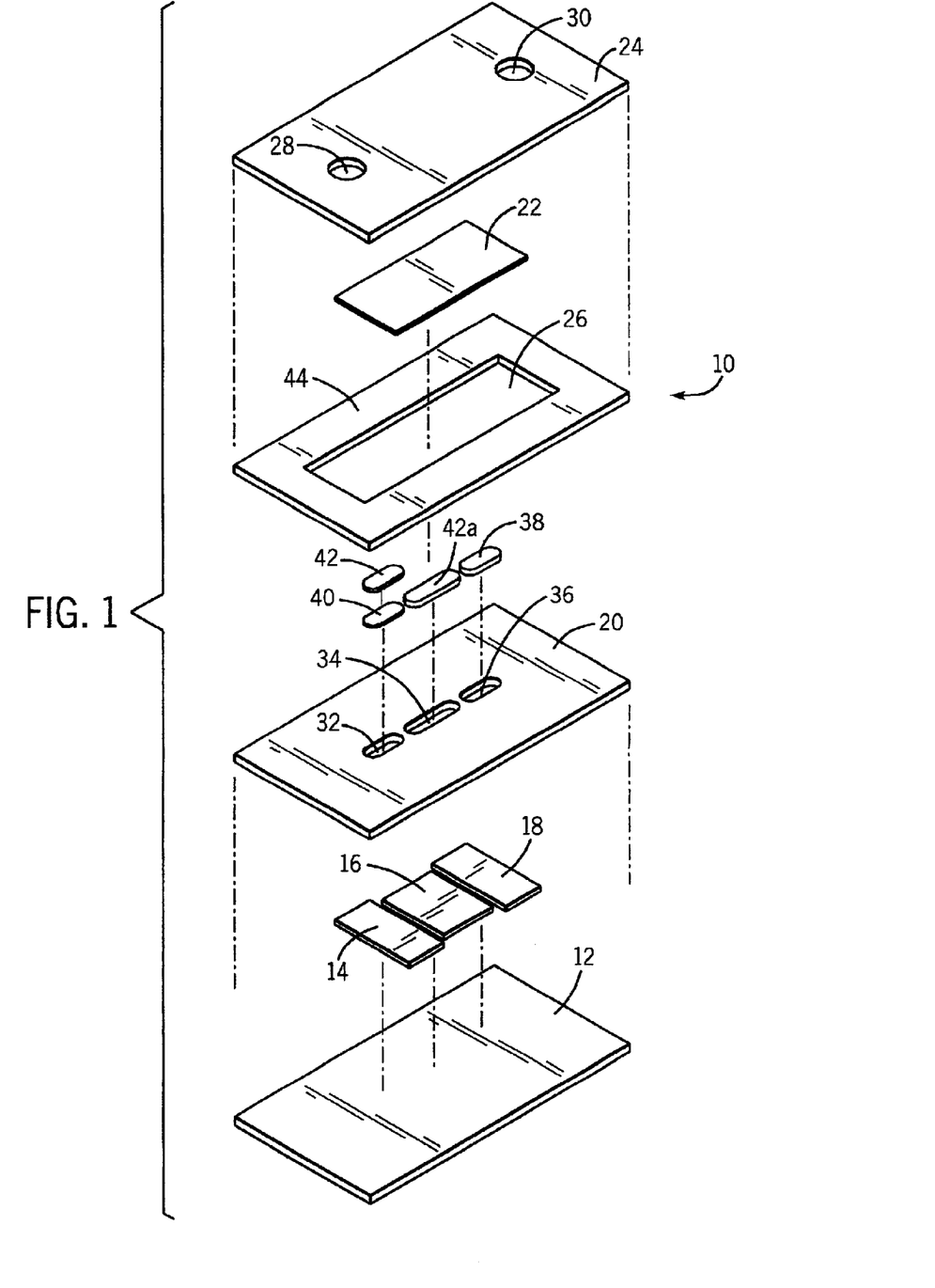
FIG. 1 is an exploded perspective view of a sensor described herein.
Figure 2:
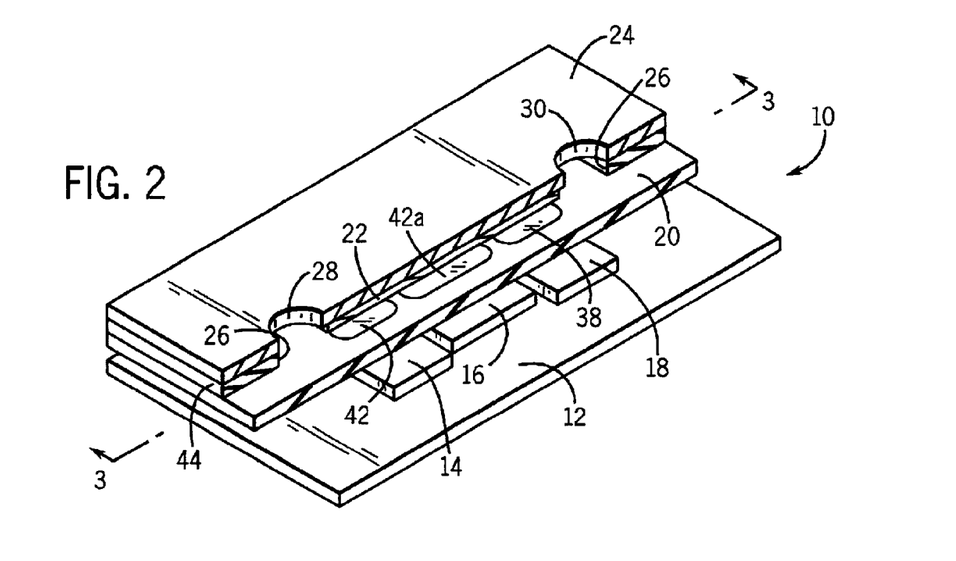
FIG. 2 is a perspective view of the sensor shown in FIG. 1. The sensor is shown as assembled, and not in exploded view. Parts of several layers are shown as being cut away in order to more clearly show parts of other layers.
Figure 3:
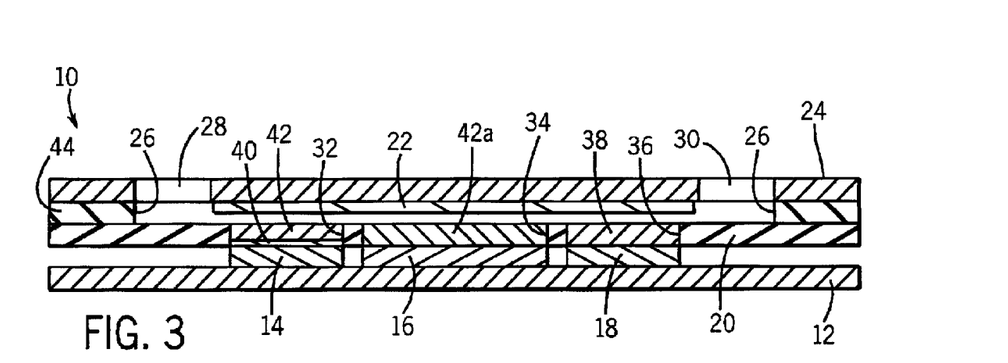
FIG. 3 is a side view in elevation of the sensor shown in FIG. 1.

Referring now to FIGS. 1, 2, and 3, a sensor 10 comprises a substrate 12, a working electrode 14, a flow rate-determining electrode 16, a reference electrode 18, an insulation layer 20, a counter electrode 22, a top layer 24, a flow channel 26, a sample inlet 28, and a sample outlet 30. Additional features 32, 34, and 36 are micro-wells formed in the insulation layer 20 to expose the working electrode 14, the flow rate-determining electrode 16, and the reference electrode 18, respectively, and to allow sufficient volume for additional layers to be formed. The sensor 10 further includes a layer 38 comprising materials deposited on the reference electrode, a reaction layer 40, a diffusion layer 42 overlying the reaction layer 40, a diffusion layer 42a overlying the flow rate-determining electrode 16, and a spacer layer 44. The portions of the working electrode 14, the flow rate-determining electrode 16, and the reference electrode 18 that are not directly under the micro-wells 32, 34, and 36, respectively, constitute the tracks and the contacts of the working electrode 14, the flow rate-determining electrode 16, and the reference electrode 18.

Typical dimensions of a sensor suitable for this invention are:

| | |
|---|---|
| major dimension of each electrode | 400 µm |
| width of flow channel | 1 mm |
| depth of flow channel | 50 µm |
| length of flow channel | 5 mm |
| support | 50–200 µm thick × 10 mm long × 6 mm wide |
| insulation layer | 40 µm thick; coextensive with the support (but does not cover the micro-wells and electrical contacts) |
| micro-wells | 30–40 µm depth × 0.4–0.8 mm long × 0.4–0.8 mm wide |
| spacer layer | 50 to 200 µm thick (area can be as great as that of the insulation layer; electrical contacts and the flow channel will be exposed) |
| top layer | 50 to 200 µm thick (area can be as great as that of the support; electrical contacts will be exposed) |
| sample inlet | 1 mm diameter |
| sample outlet | 1 mm diameter |

In addition, the process for manufacturing the sensor dictates the spacing between the electrodes. In this invention, a separation of 100 micrometers can be achieved between any two electrodes.

Materials that are suitable for preparing the substrate 12 include, but are not limited to, any non-conducting material, such as, for example, glass and polymeric materials. A polymeric material that is preferred for the substrate 12 is polyimide. Polyimide is flexible and is able to withstand the extreme temperatures encountered during fabrication of the biosensor. Other polymeric materials that are suitable for preparing the substrate include polycarbonate and polyester (e.g., "MYLAR").

The sensor preferably employs four electrodes, namely, a working electrode 14, a flow rate-determining electrode 16, a reference electrode 18, and a counter electrode 22. Alternatively, a single electrode that performs both the function of the reference electrode and the function of the counter electrode can replace the reference electrode and the counter electrode. In addition, a dummy electrode or a blank electrode can be used to compensate for interference from electrochemically active species. The reagent(s) specific to the analyte of interest is required to be deposited on the working electrode 14.

Materials that are preferred for forming the working electrode 14 and the flow rate-determining electrode 16 include, but are not limited to, conductive material, such as, for example, conductive metals, preferably noble metals. Metals that are preferred for preparing the working electrode 14 and the flow rate-determining electrode 16 include platinum, gold, and palladium, with platinum being preferred. Platinum provides a better surface for measuring hydrogen peroxide than do other metals. For example, platinum surpasses gold with respect to the properties of the voltage required for the measurement of hydrogen peroxide and the efficiency of oxidation on the surface of the working electrode.

It is preferred to deposit the metal for forming the working electrode 14, the flow rate-determining electrode 16, and the reference electrode 18 by means of vacuum deposition. Vacuum deposition is a technique that can be used to deposit a very thin, but uniform, layer of metal upon a substrate. The metal is vaporized, and the vaporized metal is deposited on the substrate. Because metals have a high boiling point, the vacuum also helps to reduce the boiling point. Vacuum deposition provides a clean uniform surface, as compared with deposition by means of screen printing. Pure metal is used for vacuum deposition; hence, there is no contamination of the surface by resins or other coating aids. It is preferred that the substrate 12 have a coarse surface (e.g., having an average surface coarseness of less than 10 micrometers) or that the electrodes deposited on the substrate 12 be electrochemically etched after deposition so that the surface areas of the electrodes have increased areas to provide increased sensitivity.

The reference electrode 18 contains a layer comprising a mixture of silver and silver chloride. This layer can be fabricated by depositing silver by electrochemical deposition on an electrode made of a conductive material, such as, for example, platinum, and then electrochemically (galvanically) treating the deposited silver in the presence of potassium chloride to obtain a layer of silver chloride.

The counter electrode 22 can be formed from any conductive material, such as carbon, gold, palladium, platinum or stainless steel. In an alternative to the use of a reference electrode and a counter electrode, one can use a dual-purpose electrode, wherein a silver layer, with or without any silver chloride, can be used to perform the functions of the reference electrode and the counter electrode. The dual-purpose electrode is not preferred, but can be used when the currents generated are low and the duration of monitoring is short. If the duration of monitoring is too long, e.g., more than one hour, the reference voltage tends to drift over time.

The flow rate-determining electrode 16 comprises a metallic electrode that can oxidize hydrogen peroxide. Metals that are suitable for the flow rate-determining electrode include, but are not limited to, platinum, palladium, and gold. The flow rate-determining electrode 16 does not contain a reaction layer. However, the flow rate-determining electrode 16 can have a diffusion layer to inhibit molecules of protein from fouling the surface of the flow rate-determining electrode.

The insulation layer 20 can be formed from any photopolymerizable material, e.g., a photoresist material. A photoresist material that is suitable for use as an insulation layer in this invention has the trademark "VACREL". Other photoresist materials that are suitable for forming the insulation layer 20 include "TENTMASTER" and "PYRALAUX". As an alternative to the use of a photopolymerizable material, the insulation layer 20 can comprise a tape having openings therein to allow the working electrode 14, the flow rate-determining electrode 16, the reference electrode 18, and the contacts to be exposed.

In the embodiment shown in FIGS. 1, 2, and 3, the top layer 24 can be made from materials that are suitable for preparing the substrate 12. As stated previously, these materials include, but are not limited to, any non-conducting material, such as, for example, glass and polymeric materials. A polymeric material that is preferred for the top layer 24 is polyimide. Polyimide is flexible and is able to withstand the extreme temperatures encountered during fabrication of the biosensor. Other polymers that can be used to form the top layer 24 include polyvinyl chloride and polyester. In an alternative embodiment, the counter electrode 22 can be lengthened and used as the top layer. In this alternative embodiment, the sample inlet and the sample outlet would have to be formed in the counter electrode. In another alternative embodiment, the material for the counter electrode 22 can be deposited on the top layer 24 by means of vacuum deposition. As stated previously, vacuum deposition is a technique that can be used to deposit a very thin, but uniform, layer of metal upon a substrate. The metal is vaporized, and the vaporized metal is deposited on the substrate. Because metals have a high boiling point, the vacuum also helps to reduce the boiling point.

The sample inlet 28 is the position at which the sample is introduced into the sensor 10. The sample inlet 28 is preferably placed in register with the working electrode 14. The sample outlet 30 is the position at which the sample is removed from the sensor 10. The sample outlet is preferably placed downstream of the reference electrode 18. The sample flows through the flow channel 26, which begins at the sample inlet 28 and terminates at the sample outlet 30.

As stated previously, the micro-wells 32, 34, and 36 are formed in the insulating layer 20 to expose the working electrode 14, the flow rate-determining electrode 16, and the reference electrode 18, respectively. In addition, the materials that form the reaction layer 40 and the diffusion layer 42 are inserted in the micro-well 32. The materials that form the diffusion layer 42a are inserted in the micro-well 34. The materials that form the layer 38 are inserted in the micro-well 36. The materials that form the layer 38 are substantially similar to the materials that form the layers 42 and 42a.

The reaction layer 40 comprises an enzyme immobilized in a polymeric matrix, so that the enzyme will not diffuse from the reaction layer as the biosensor is being used. The reaction layer 40 can be formed by polymerizing monomeric material, such as, for example, methacrylate or a derivative thereof, in the presence of enzyme in a suitable reaction medium. The enzyme is physically trapped in the polymeric matrix, and hence, is immobilized. Any enzyme that is capable of generating an electrochemically active reaction product, such as hydrogen peroxide, can be used in the biosensor of this invention. Representative examples of such enzymes include, but are not limited to, alcohol oxidase, cholesterol oxidase, glucose oxidase, glutamate oxidase, and lactate oxidase. The enzyme(s) is immobilized on the surface of the working electrode 14. The depth of the reaction layer 40 preferably ranges from about 10 to about 15 micrometers.

The flow rate-determining electrode 16 may contain an optional blank layer (not shown), which layer has a depth substantially equal to the reaction layer 40, so that the depth of the flow channel 26 does not vary significantly from the working electrode 14 to the flow rate-determining electrode 16.

The diffusion layer 42 controls the flux of molecules from one major surface of the layer to the other major surface of the layer. The diffusion layer 42 provides a barrier to the free flow of material. The diffusion layer 42 will prevent molecules that are greater in size than the pores of the diffusion layer 42 from flowing through the diffusion layer 42, but will allow molecules that are smaller in size than the pores of the diffusion layer 42 to flow through the diffusion layer 42. The diffusion layer 42 comprises a nonreactive polymeric matrix that provides a tortuous path through which the analyte diffuses from the flow channel 26 to the reaction layer 40. This tortuous path allows only a fraction of the analyte in the sample to diffuse to the reaction layer 40. The diffusion layer 42 retains all macromolecules, such as protein, on the surface of the diffusion layer 42. The diffusion layer 42 limits the number of molecules of the analyte that can reach the reaction layer 40, and, consequently, limits the rate of oxidation of the analyte. This partial conversion of the analyte at the working electrode 14 helps to increase the dynamic range of the sensor 10. In a non-mediated biosensor, i.e., a biosensor that does not employ a mediator, the rate of reaction is dependent upon the level of oxygen dissolved in the sample. Because only a fraction of the analyte reaches the reaction layer 40, and because oxygen can diffuse faster than can the analyte, the diffusion layer 42 makes it possible to use the biosensor over a wider range of concentrations than can be used with a biosensor that does not have the diffusion layer 42. The diffusion layer 42 can be formed by polymerizing monomeric material, such as, for example, methacrylate or a derivative thereof, in a suitable reaction medium.

The diffusion layer 42a is identical, or substantially identical, to the diffusion layer 42. The diffusion layer 42a retains all macromolecules, such as protein, on the surface of the diffusion layer 42a, thereby preventing these macromolecules from fouling the surface of the flow rate-determining electrode 16. The optional diffusion layer 38 is identical, or substantially identical, to the diffusion layer 42. The optional diffusion layer 38 retains all macromolecules, such as protein, on the surface of the diffusion layer 38, thereby preventing these macromolecules from fouling the surface of the reference electrode 18.

The spacer layer 44 is inserted between the top layer 24 and the insulating layer 20 for the purpose of creating a flow channel 26 through which the sample flows during an assay. Materials that are suitable for forming the spacer layer 44 include, but are not limited to, pressure sensitive adhesive tape having an adhesive layer on both major surfaces thereof.

The flow rate-determining electrode 16 performs the function of determining the rate of flow of a sample of fluid. This function can be carried out in a variety of ways. In one embodiment, the working electrode comprises a reaction layer and a diffusion layer. The flow rate-determining electrode comprises a diffusion layer and, optionally, a blank layer. In this embodiment, the responses from the working electrode and the flow rate-determining electrode are measured at selected known rates of flow of fluid, and a calibration curve is established to correlate the aforementioned responses with the known rates of flow of fluid. In this embodiment, for flow rates that are not known, the response of the working electrode and the response of the flow-rate determining electrode are measured and the rate of flow is determined from the aforementioned calibration data.

In another embodiment, the working electrode comprises a reaction layer, a diffusion layer, and a layer of material that converts electrochemically active material (e.g., hydrogen peroxide) to non-reactive material (e.g., oxygen and water), e.g., catalase, peroxidase. Because peroxidase requires a reducing agent, such as, for example, phenol or aniline, to reduce the oxidized enzyme, catalase is preferred over peroxidase where additional reducing agent cannot be used. The layer of material that converts electrochemically active material to non-reactive material typically has a thickness of about five micrometers. The flow rate-determining electrode comprises a reaction layer and a diffusion layer. The layer of material that converts hydrogen peroxide to oxygen and water will oxidize hydrogen peroxide molecules that diffuse to the flow channel, thereby eliminating the back diffusion of hydrogen peroxide to the working electrode. In this embodiment, the responses from the working electrode and the flow rate-determining electrode are measured at selected known rates of flow of fluid, and a calibration curve is established to correlate the aforementioned responses with the known rates of flow of fluid. In this embodiment, for flow rates that are not known, the response of the working electrode and the response of the flow-rate determining electrode are measured and the rate of flow is determined from the aforementioned calibration data.

In still another embodiment, two flow rate-determining electrodes and one working electrode are employed. The working electrode comprises a reaction layer and a diffusion layer. Each of the flow rate-determining electrodes comprises a diffusion layer and, optionally, a blank layer. The working electrode is placed between the two flow rate-determining electrodes. In this embodiment, the responses from the working electrode and each of the flow rate-determining electrodes are measured at selected known rates of flow of fluid, and a calibration curve is established for each flow rate-determining electrode and the working electrode to correlate the aforementioned responses with the known rates of flow of fluid. In this embodiment, for flow rates that are not known, the response of the working electrode and the response of the flow-rate determining electrode are measured and the rate of flow is determined from the aforementioned calibration data. In this embodiment, in addition to the capability of determining the rate of flow of fluid, the direction of flow of fluid can also be determined. Depending on the direction of flow of the fluid, only one of the flow rate-determining electrodes will generate a measurable response. By knowing which flow rate-determining electrode generates the measurable response, the direction of flow of fluid can be determined. The biosensor of the third embodiment can be used in conjunction with micro-machined micro-fluidic devices wherein the direction of the flow is important. In such a device, various means, such as, for example, valves or electro-osmotic components, are used to control the direction of the flow of the fluid. If the fluid is not flowing in the proper direction, the desired effect will not occur. For example, if one is trying to carry out a reaction in a micro-machined laboratory in a chip, then the reactants will not be delivered to the proper location in accordance with the proper sequence. Knowledge of the direction of flow of the fluid will ensure the proper sequence of process steps.

The sensor 10 can optionally have a dummy electrode to compensate for interference from electrochemically active species. If a dummy electrode is used, it is preferably placed upstream of the working electrode 14.

The sensor 10 can also optionally include a semi-permeable, preferably polymeric, layer (not shown), such as, for example, a polydiaminobenzene layer, located between the surface of the working electrode 14 and the layer of reactive material 40. This layer is preferably formed on the surface of the working electrode 14 by electrochemical deposition. In electrochemical deposition, the polydiaminobenzene is deposited on an electrode by electrochemical polymerization of 1,3-diaminobenzene at the surface of the electrode. The polymeric film thus formed is insulating in nature. The purpose of this layer is to limit the migration and diffusion of interfering agents to the surface of the working electrode 14. Examples of interfering agents include ascorbic acid, uric acid, gentisic acid, and acetaminophen. This layer is preferred when the level of applied voltage is high. Different interfering agents have different oxidation potentials. At lower potentials, e.g., about 300 mV, only gentisic acid will contribute to the signal obtained. As the voltage increases, other interfering agents will begin to contribute to the signal obtained. The thickness of the semi-permeable layer is preferably about 100 Angstroms.

The sensor 10 can also optionally include a semi-permeable, preferably polymeric, layer (not shown), such as, for example, a polydiaminobenzene layer, located between the surface of the flow rate-determining electrode 16 and the diffusion layer 42. This optional semi-permeable layer can be identical or substantially identical to the optional semi-permeable layer applied to the working electrode 14.

The electrodes can be arranged in any order, but some orders are preferable to others. In preferred embodiments, the working electrode 14 should be positioned upstream of the flow-rate determining electrode 16. The reference electrode 18 should be positioned downstream of the flow rate-determining electrode 16 and in the flow channel 26 so that a minimum amount of time elapses between the time that the sample is excreted and the time that the sample contacts the working electrode 14.

It is preferred that the four electrodes of the sensor 10 be positioned on two substrates. As shown in FIGS. 2 and 3, one substrate preferably supports the working electrode 14, the flow rate-determining electrode 16, and the reference electrode 18. Another substrate preferably supports the counter electrode 22.

Any electrochemical device that can continuously collect data from a sensor having at least two working electrodes (i.e., a working electrode and at least one flow rate-determining electrode) and having one reference electrode and one counter electrode can be used in this invention. Such a device is known as a multipotentiostat, e.g., a bipotentiostat or a tripotentiostat. A bipotentiostat can simultaneously apply the same or different voltage to two working electrodes, with respect to a single reference electrode, in a single electrochemical cell. In a system employing a bipotentiostat, only one counter electrode is used for the measurement of the current generated at the two working electrodes. Bipotentiostats are commercially available. Echochemie (Netherlands) and PineChem Instrument Company (United States) manufacture potentiostats suitable for use in this invention. The device should have the capability of:

(1) applying a constant voltage at the working electrode and flow rate-determining electrode with respect to a single reference electrode;

(2) measuring the current generated at the working electrode and the flow rate-determining electrode by means of a single counter electrode by the oxidation of the reaction product.

A voltage of magnitude sufficient to oxidize the electrochemically active reaction product (e.g., hydrogen peroxide in the case of glucose oxidase) is applied to the working electrode 14 and the flow rate-determining electrode 16. The responses (current) from the working electrode 14 and the flow rate-determining electrode 16 are measured. It is assumed that the flow rate-determining electrode 16 measures the current that is not measured by the working electrode 14. From a calibration relationship that has been established between the rate of flow of the fluid and the responses of the working electrode 14 and the flow rate-determining electrode 16, the rate of flow of the fluid is calculated and the response of the sensor 10 is corrected from the value determined by measurement.

It may be desirable to utilize portable instruments in place of the bipotentiostat. In addition to carrying out the same functions as the bipotentiostat, the portable instruments can be designed to control parameters such as pressure (vacuum) and monitor parameters such as temperature at the time of measurement.

The sensor can be fabricated by adapting procedures employed in preparing semiconductors. A preferred method of fabrication involves the following method:

1. A photoresist layer is deposited on a first nonconducting substrate 12 (glass, polyimide, etc.).
2. The photoresist layer is developed by means of a mask in order to derive a design of the layer of metal. This design constitutes the electrodes, along with the tracks and the electrical contacts.
3. The layer of metal (e.g., platinum, gold, palladium, or some other noble metal) is deposited on the substrate 12 bearing the developed mask by means of a deposition technique, such as vapor deposition or sputtering.
4. The photoresist layer is then stripped, leaving behind the metal deposited, which will form the contacts, tracks, and the areas of the working electrode 14, the flow rate-determining electrode 16, and the reference electrode 18 located beneath the micro-wells 32, 34, and 36.
5. A second photoresist layer is deposited on the substrate 12, which contains the metal deposited previously, in the manner previously described, i.e., by means of a mask, to expose the areas of the deposited metal that will constitute the working electrode 14, the flow rate-determining electrode 16, and the reference electrode 18. The developed photoresist remaining forms the insulation layer 20. Micro-wells 32, 34, and 36 are formed so as to be in register with the areas of the working electrode 14, the flow rate-determining electrode 16, and the reference electrode 18, where additional layers of material are to be deposited. The second photoresist layer defines the micro-well 32, which in turn defines the area of the working electrode 14 that contains the reaction layer 40 and the diffusion layer 42; the second photoresist layer defines the micro-well 34, which in turn defines the area of the flow rate-determining electrode 16 that contains the diffusion layer 42a and, optionally, a blank layer; and the second photoresist layer defines the micro-well 36, which in turn defines the area of the reference electrode 18 that contains a layer of silver/silver chloride, and, optionally, a diffusion layer.
6. Silver is galvanically deposited in the micro-well 36 overlying the reference electrode 18 and then partially converted to silver chloride by galvanically treating the deposited silver in the presence of potassium chloride.
7. The enzyme (e.g., glucose oxidase) is mixed with photopolymerizable monomer, such as methacrylate or a derivative thereof, in a hydrophilic solvent and dispensed to the micro-well 32 overlying the working electrode 14. The chemical formulation is exposed to ultraviolet radiation to immobilize the enzyme in a polymeric (e.g., polymethacrylate) reaction layer 40.
8. A polymeric (e.g., polymethacrylate) diffusion layer 42 is dispensed to the micro-well 32 overlying the working electrode 14. This layer 42 is also formed in a manner similar to that used to form the reaction layer 40. This layer is similar to the enzyme-containing reaction layer 40, but does not contain the enzyme. This diffusion layer 42 allows wider dynamic range and also separates the proteins that may be present in the sample.
9. A polymeric diffusion layer 42a is dispensed to the micro-well 34 overlying the flow rate-determining electrode 16. This layer 42a is also formed in a manner similar to that used to form the reaction layer 40. This layer is similar to the enzyme-containing reaction layer 40, but does not contain the enzyme. This diffusion layer 42a allows wider dynamic range and also separates the proteins that may be present in the sample. A blank layer (not shown) may be optionally dispensed to the micro-well 34 prior to the dispensing of the diffusion layer 42a.
10. A spacer layer 44 is then placed on the assembly as shown in FIG. 1. A spacer layer 44 suitable for use in the biosensor of this invention is a layer of double-sided pressure sensitive adhesive tape (50 $\mu$m thick).
11. A plate of a conductive metal (e.g., gold, stainless steel, platinum, palladium) is placed over the spacer layer 44, thereby forming the counter electrode 22. The counter electrode 22 and the spacer layer 44 form a flow channel 26. In an alternative embodiment, as shown in FIG. 1, an insulating support can be placed over the counter electrode 22. The insulating support is the top layer 24. In another alternative embodiment, the counter electrode 22 can be deposited on an insulating support, such as polyester ("MYLAR"), and the insulating support bearing the deposited counter electrode 22 can be placed over the spacer layer 44. If an insulating support is not employed, the sample inlet and the sample outlet will have to be formed in the plate of conductive metal that forms the counter electrode. If an insulating support is employed, as shown in FIG. 1, the sample inlet and the sample outlet will have to be formed in the insulating support. If the counter electrode 22 is deposited on an insulating support, as described in the third embodiment of this step, the sample inlet and the sample outlet will have to be formed in the insulating support and in the deposited counter electrode if the counter electrode would prevent the sample form obtaining access to the flow channel.

If the embodiment requires a layer of material that converts hydrogen peroxide to oxygen and water, e.g., catalase, for the micro-well 32, this layer can be applied by dispensing the material for forming this layer to the micro-well in the same manner as the diffusion layer 42. The material can be dispensed immediately after the material for forming the diffusion layer 42 is dispensed.

In order to use the sensor of this invention for the analysis of a biological sample, i.e., as a biosensor, an artificial opening will be made in the skin of a body part (for example, arm or abdomen) for extracting body fluid, which constitutes the biological sample. Means for forming openings in the skin are well known to those skilled in the art. Examples of these means include, but are not limited to, laser poration, puncturing by means of microneedles.

The sensor 10 can be placed in an insulating attachment (not shown) that has two openings. The sample inlet 28 and the sample outlet 30 will be aligned with these openings in the attachment, and the sensor 10 can be secured to the device with the aid of alignment rings. One of the openings in the attachment will serve as the inlet. The other opening in the attachment will serve as the outlet. This outlet is also connected to a reservoir, where the used sample is stored. The outlet is also connected to a vacuum generator that will create the necessary pressure difference for the sample to flow out of the artificial opening in the skin of the body part. The attachment can be fastened to the body part by means of a pressure-sensitive adhesive, such as, for example, double-sided adhesive tape.

The sample extracted from the body part will enter the flow channel 26 through the inlet of the attachment and the inlet 28 of the sensor 10, flow over the arrangement of electrodes, and emerge from the outlet 30 of the sensor and the outlet of the attachment. The expended sample will be stored in the reservoir until it is discarded.

The sensor and method of this invention can be used for situations where the analyte is also electrochemically active. For example, if one were to use an oxygen electrode (i.e., an electrode that measures the reduction of oxygen) in the above situation, the concentration profile of oxygen could be used as a monitor of the rate of flow. Oxygen electrodes can be conveniently used for the electrochemical determination of oxygen in a sample. Oxygen is consumed in the reaction where oxidation of glucose is catalyzed by glucose oxidase. The drop in the oxygen tension (i.e., concentration of oxygen dependent upon the level of oxygen at the surface of a fluid) resulting from the oxidation of glucose is directly proportional to the concentration of glucose. The principle employed in the measurement of oxygen is similar to the principle employed in the measurement of hydrogen peroxide. The measurement of hydrogen peroxide is related to the generation of the reaction product (hydrogen peroxide) and the measurement of oxygen is related to the consumption of the reactant (oxygen). The concentration of hydrogen peroxide will increase as the concentration of glucose increases and the concentration of oxygen will decrease as the concentration of glucose increases. In a situation where an oxygen electrode is used, typical conditions would include a platinum cathode (where oxygen is reduced according to the reaction $O_2+4H^++4e^-\rightarrow 2H_2O$), and a Ag/AgCl dual-purpose electrode wherein a potential of –0.6 V is applied to the platinum cathode, and a current proportional to the concentration of oxygen would be produced).

The sensor and method of this invention are particularly applicable to continuous monitoring biosensors that involve the measurement of a reaction product or a reactant as a means for determining the concentration of an analyte in a biological sample. For example, the sensor and method of this invention provide a method for determining the concentration of an analyte in a sample of fluid, wherein said sample flows at an unknown rate of flow. The method comprises the steps of providing a sensor having a working electrode made of platinum, a flow-rate determining electrode made of platinum, a reference electrode, and a counter electrode. Alternatively, the reference electrode and the counter electrode can be replaced by a dual-purpose electrode (i.e., counter/reference electrode) made of Ag/AgCl. The sample of fluid is then introduced to the flow channel of the sensor. Then, the response of the working electrode and the response of the flow rate-determining electrode are determined at the unknown rate of flow of the sample. The value of the unknown rate of flow of the sample is determined by means of a calibration relationship. Such a calibration relationship has been described previously. The uncorrected value of the concentration of the analyte in the sample is determined by means of a calibration relationship. Methods for developing calibration relationships for correlating the concentration of an analyte with an electrical response are well known to those of ordinary skill in the art. For example, the response of the working electrode can be correlated with the concentration of analyte by running a series of calibration runs in which samples of fluid containing various concentrations of analyte are introduced to the sensor at a rate of flow of sample that is expected to be the average rate of flow of the sample. The corrected value of the concentration of the analyte in the sample is determined by correcting the value of the uncorrected concentration of the analyte by means of a calibration relationship that correlates the rate of flow of fluid determined previously by adjusting the value of the concentration of the analyte with a factor determined by another set of calibration runs. For example, if the rate of flow of fluid is higher than the average rate of flow, the calibration relationship will probably result in an upward adjustment of the value of the concentration of the analyte; if the rate of flow of fluid is lower than the average rate of flow, the calibration relationship will probably result in a downward adjustment of the value of the concentration of the analyte.

The biosensor is designed for use with human patients. The biological sample can be drawn from the body of the patient by forming an artificial opening on the skin and by applying a vacuum to aid in drawing the interstitial fluid from the body of the patient, whereby the interstitial fluid can contact the electrodes of the biosensor. The concentration of the analyte, e.g., glucose, in the interstitial fluid can thus be determined.

The following non-limiting examples, will further illustrate this invention.

EXAMPLES

Example 1

This example illustrates a sensor suitable for monitoring the concentration of glucose in a biological sample with the additional capability of measuring the rate of flow of the biological sample. In this example, the working electrode is placed upstream of the flow rate-determining electrode. The sample passes over the working electrode before it contacts the flow rate-determining electrode.

The sensor comprises a working electrode made of platinum, a flow-rate determining electrode made of platinum, a reference electrode, and a counter electrode. Alternatively, the reference electrode and the counter electrode can be replaced by a dual-purpose electrode (i.e., counter/reference electrode) made of Ag/AgCl. The working electrode and the flow rate-determining electrode have deposited thereon a semi-permeable membrane to suppress interferences from electrochemically active interfering materials in the biological sample. Overlying the working electrode is a hydrogel membrane, which can contain up to three distinct layers. The layer of the hydrogel membrane closest to the surface of the working electrode is the reaction layer, which layer contains glucose oxidase. Overlying the reaction layer containing glucose oxidase is a diffusion layer. Overlying the flow rate-determining electrode is a hydrogel membrane, which can contain up to three distinct layers. The layer of the hydrogel membrane closest to the surface of the flow rate-determining electrode is a blank layer, which is identical, or substantially identical, to the reaction layer overlying the working electrode, with the exception that glucose oxidase is not present. Overlying the blank layer is a diffusion layer.

In the embodiment described in this example, a catalase layer is not deposited over either the working electrode or the flow rate-determining electrode.

Figure 7:
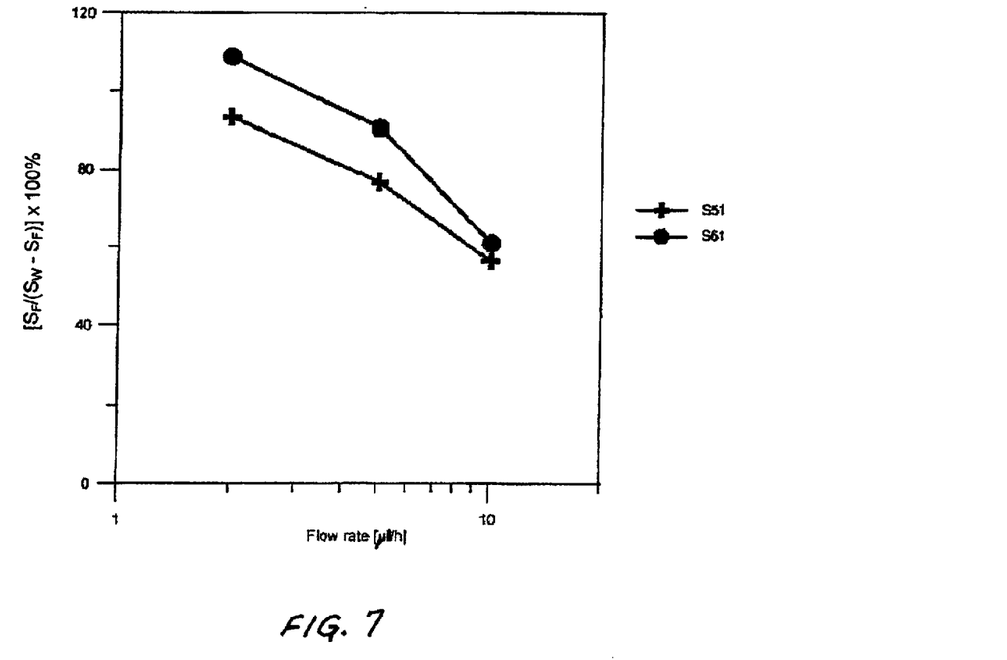
FIG. 7 is a graph showing the calibration relationship of a sensor of the type shown in FIG. 4.

The concentration profile of hydrogen peroxide in the flow channel is shown in FIG. 4. In FIG. 4, the working electrode is designated by the reference numeral 100, the flow rate-determining electrode is designated by the reference numeral 102, and the flow channel is designated by the reference numeral 104. The concentration profile is designated by the dotted lines. The results obtained, as shown in FIG. 7, show that the ratio of the response of the flow rate-determining electrode ($S_F$) to the difference in the response of the working electrode ($S_W$) and the response of the flow rate-determining electrode ($S_F$) is inversely related to the rate of flow. Maximum sensitivity to changes in the rate of flow ranges from about 2 to about 10 $\mu$l/hr.

The formulation for the reaction layer of the working electrode is prepared as follows. Glucose oxidase is dissolved in deionized water (25 wt %) and mixed with an equal amount of polyethylene glycol 400 containing N-methyl iminodiethanol (1 wt %) and benzoquinone (0.2 wt %). A precursor solution was prepared containing photoinitiator (2,2'dimethoxyphenyl acetophenone, 1 wt %), crosslinking agent (tetraethylene glycol dimethacrylate, 3 wt %), reactive monomer (2-hydroxyethylmethacrylate, 12 wt %), filler (poly(2-hydroxymethacrylate), 24 wt %), plasticizer (polyethylene glycol 400, 36 wt %), and deionized water (24 wt %). One (1) part of the enzyme solution is then mixed with three (3) parts of the precursor solution.

The foregoing solution is dispensed to the micro-well that is in register with the working electrode, and the mixture is photopolymerized by exposure to ultraviolet radiation to form the reaction layer of the working electrode. The diffusion layer is formed in a similar manner, but the enzyme solution is omitted. The diffusion layer overlies the reaction layer.

Example 2

This example illustrates a sensor suitable for monitoring the concentration of glucose in a biological sample with the additional capability of measuring the rate of flow of the biological sample. In this example, the working electrode is placed upstream of the flow rate-determining electrode. The sample passes over the working electrode before it contacts the flow rate-determining electrode.

The sensor comprises a working electrode made of platinum, a flow-rate determining electrode made of platinum, a reference electrode, and a counter electrode. Alternatively, the reference electrode and the counter electrode can be replaced by a dual-purpose electrode (i.e., counter/reference electrode) made of Ag/AgCl. The working electrode and the flow rate-determining electrode have deposited thereon a semi-permeable membrane to suppress interferences from electrochemically active interfering materials in the biological sample. Overlying the working electrode is a hydrogel membrane, which can contain up to three distinct layers. The layer of the hydrogel membrane closest to the surface of the working electrode is the reaction layer, which layer contains glucose oxidase. Overlying the layer containing glucose oxidase is a diffusion layer. Overlying the flow rate-determining electrode is a hydrogel membrane, which can contain up to three distinct layers. The layer of the hydrogel membrane closest to the surface of the flow rate-determining electrode is identical, or substantially identical, to the reaction layer overlying the working electrode. Overlying the blank layer is a diffusion layer.

The layer of the hydrogel membrane furthest from the surface of the working electrode contains catalase, which converts hydrogen peroxide to oxygen, in order to prevent leakage of hydrogen peroxide to the flow channel. The catalase layer is deposited on only over the working electrode.

Figure 8:
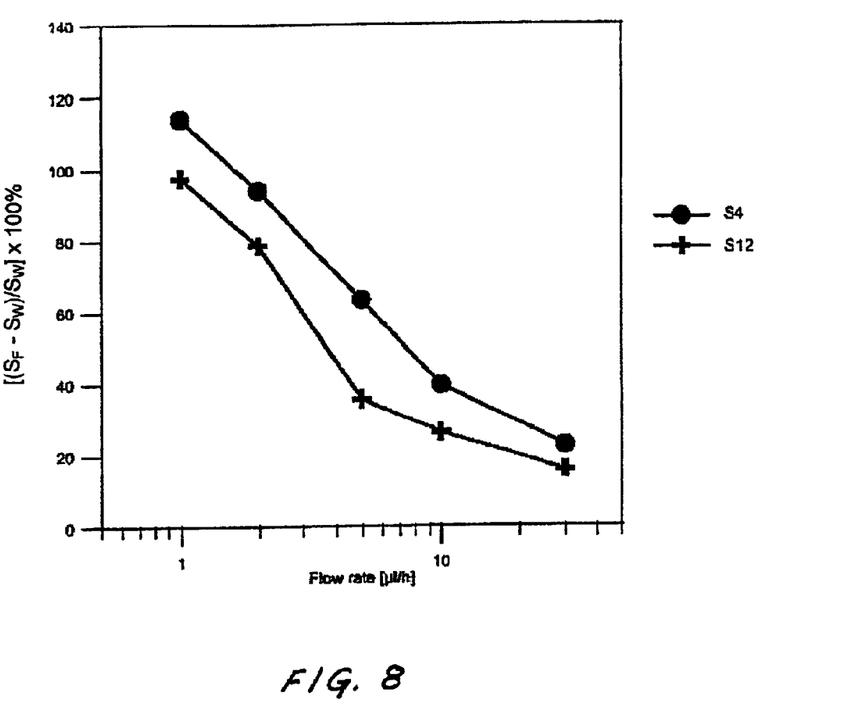
FIG. 8 is a graph showing the calibration relationship of a sensor of the type shown in FIG. 5.

The concentration profile of hydrogen peroxide in the flow channel is shown in FIG. 5. In FIG. 5, the working electrode is designated by the reference numeral 200, the flow rate-determining electrode is designated by the reference numeral 202, and the flow channel is designated by the reference numeral 204. The concentration profile is designated by the dotted lines. The results obtained, as shown in FIG. 8, show that the ratio of the difference in the response of the flow-rate determining electrode ($S_F$), which does not have the catalase layer, and the response of the working electrode ($S_W$), which does have the catalase layer, to the response of the working electrode ($S_W$) is inversely related to the rate of flow. Maximum sensitivity to changes in the rate of flow ranges from about 2 to about 10 $\mu$l/hr.

Example 3

This example illustrates a biosensor in which two flow rate-determining electrodes are used. The working electrode can be positioned such that the sample passes over a first flow-rate determining electrode prior to contacting the working electrode. After contacting the working electrode, the sample passes over a second flow rate-determining electrode.

The working electrode comprises the same materials and has substantially similar overlying layers as does the working electrode of Example 1. The flow rate-determining electrodes comprise the same materials and have the substantially similar overlying layers as do the flow rate-determining electrodes of Example 1. The counter electrode and the reference electrode comprise the same materials and have the substantially similar overlying layers as do the counter electrode and the reference electrode of Example 1.

In the embodiment of this example, both the flow rate and direction of flow of the sample can be determined. In order to perform measurements of responses from the electrodes, a tripotentiostat is employed. If no measurable signal can be obtained from one of the flow rate-determining electrodes, it can be assumed that that electrode is upstream of the working electrode, and that the fluid is flowing toward the other flow rate-determining electrode.

The concentration profile of hydrogen peroxide in the flow channel is shown in FIG. 6. In FIG. 6, the working electrode is designated by the reference numeral 300, the flow rate-determining electrodes are designated by the reference numerals 302 and 303, and the flow channel is designated by the reference numeral 304. The concentration profile is designated by the dotted lines.

Example 4

This example illustrates a way in which the principle of this invention can be used to determine the rate of flow of a fluid containing an analyte present at a known concentration.

This example can be adapted to a situation of the type where a biological sample, e.g., a drug, a nutrient (e.g., glucose) is to be infused into the body of a patient. Because the concentration of the analyte is already known, the concentration need not be measured; however, the rate of flow of fluid may be desired in order to determine the quantity of analyte that is infused. Accordingly, a working electrode is not required. Because hydrogen peroxide must still be generated, the flow rate-determining electrode requires a reaction layer.

In this example, the sensor comprises a flow rate-determining electrode made of platinum, a reference electrode, and a counter electrode. Alternatively, the reference electrode and the counter electrode can be replaced by a dual-purpose electrode made of Ag/AgCl. The flow rate-determining electrode has deposited thereon a semi-permeable membrane to suppress interferences from electrochemically active interfering materials in the biological sample. Overlying the flow rate-determining electrode is a hydrogel membrane, which can contain up to three distinct layers. The layer of the hydrogel membrane closest to the surface of the working electrode is a reaction layer, which layer contains glucose oxidase. Overlying the layer containing glucose oxidase is a diffusion layer.

The concentration of the analyte is measured by a method that does not involve the sensor. The fluid is introduced to the sensor and the response from the flow-rate determining electrode is measured. A relationship that has been previously established to correlate responses of the sensor, the concentrations of the analyte, and rates of flow of fluid can be used to determine an unknown rate of flow of the sample of fluid.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A sensor for determining the rate of flow of a fluid containing an analyte of interest, comprising a channel through which said fluid flows, said channel constructed so that said fluid is capable of coming into contact with:
   (a) a working electrode, wherein a reaction layer overlies said working electrode and said reaction layer contains a reagent that reacts with the analyte of interest;
   (b) at least one flow rate-determining electrode;
   (c) a reference electrode; and
   (d) a counter electrode.

2. The sensor of claim 1, wherein a diffusion layer overlies said reaction layer.

3. The sensor of claim 2, wherein said reagent that reacts with the analyte of interest includes an enzyme.

4. The sensor of claim 3, wherein said enzyme is an oxidase.

5. The sensor of claim 4, wherein said enzyme is selected from the group consisting of alcohol oxidase, cholesterol oxidase, glucose oxidase, glutamate oxidase, and lactate oxidase.

6. The sensor of claim 1, wherein a semi-permeable layer is placed between said working electrode and said reaction layer.

7. The sensor of claim 1, wherein a diffusion layer overlies said at least one flow rate-determining electrode.

8. The sensor of claim 7, wherein a semi-permeable layer is placed between said at least one flow rate-determining electrode and said diffusion layer.

9. The sensor of claim 1, wherein a diffusion layer overlies said reaction layer, and a layer of material that converts electrochemically active material to non-reactive material overlies said diffusion layer.

10. The sensor of claim 9, wherein a semi-permeable layer is placed between said working electrode and said reaction layer.

11. The sensor of claim 9, wherein a second reaction layer overlies said at least one flow rate-determining electrode and a diffusion layer overlies said second reaction layer.

12. The sensor of claim 11, wherein a semi-permeable layer is placed between said at least one flow rate-determining electrode and said second reaction layer.

13. The sensor of claim 1, wherein two flow rate-determining electrodes are employed, one of said flow rate-determining electrodes being upstream of said working electrode and the other of said flow rate-determining electrodes being downstream of said working electrode.

14. A method for determining the rate of flow of a sample of fluid in a sensor having a channel, wherein said sample of fluid flows in said channel, said method comprising the steps of:
   (a) providing the sensor of claim 1;
   (b) determining responses of said working electrode and responses of said flow rate-determining electrode at known rates of flow of fluid;
   (c) establishing a relationship between said responses measured in step (b) and said rates of flow of fluid in step (b);
   (d) determining the response of said working electrode and the response of said flow rate-determining electrode at an unknown rate of flow of said sample of fluid; and
   (e) determining the value of said unknown rate of flow of said sample of fluid by means of said relationship established in step (c).

15. The method of claim 14, wherein said responses result from the formation of an electrochemically active material.

16. The method of claim 15, wherein said electrochemically active material is hydrogen peroxide.

17. The method of claim 15, wherein said electrochemically active material is oxygen.

18. A method for determining the concentration of an analyte in a sample of fluid, wherein said sample of fluid flows at an unknown rate of flow, said method comprising the steps of:
   (a) providing the sensor of claim 1;
   (b) introducing said sample of fluid to said flow channel of said sensor, said rate of flow of said sample being unknown;
   (c) determining the response of said working electrode and the response of said flow rate-determining electrode at said unknown rate of flow of said sample of fluid;
   (d) determining the value of said unknown rate of flow of said sample of fluid by means of a calibration relationship;
   (e) determining the uncorrected value of concentration of said analyte in said sample of fluid by means of a calibration relationship; and
   (f) determining the corrected value of concentration of said analyte in said sample of fluid by correcting said value of uncorrected concentration of said analyte by means of said rate of flow determined in step (d).

19. A sensor for determining the rate of flow of a fluid containing an analyte of interest, comprising a channel through which said fluid flows, said channel constructed so that said fluid is capable of coming into contact with:
  (a) a working electrode, wherein a reaction layer overlies said working electrode and said reaction layer contains a reagent that reacts with the analyte of interest;
  (b) at least one flow rate-determining electrode; and
  (c) a dual-purpose electrode that performs the functions of a reference electrode and a counter electrode.

20. The sensor of claim 19, a diffusion layer overlies said reaction layer.

21. The sensor of claim 20, wherein said reagent that reacts with the analyte of interest includes an enzyme.

22. The sensor of claim 21, wherein said enzyme is an oxidase.

23. The sensor of claim 21, wherein said enzyme is selected from the group consisting of alcohol oxidase, cholesterol oxidase, glucose oxidase, glutamate oxidase, and lactate oxidase.

24. The sensor of claim 19, wherein a semi-permeable layer is placed between said working electrode and said reaction layer.

25. The sensor of claim 19, wherein a diffusion layer overlies said at least one flow rate-determining electrode.

26. The sensor of claim 25, wherein a semi-permeable layer is placed between said at least one flow rate-determining electrode and said diffusion layer.

27. The sensor of claim 19, wherein a diffusion layer overlies said reaction layer, and a layer of material that converts electrochemically active material to non-reactive material overlies said diffusion layer.

28. The sensor of claim 27, wherein a semi-permeable layer is placed between said working electrode and said reaction layer.

29. The sensor of claim 27, wherein a second reaction layer overlies said at least one flow rate-determining electrode and a diffusion layer overlies said second reaction layer.

30. The sensor of claim 29, wherein a semi-permeable layer is placed between said at least one flow rate-determining electrode and said second reaction layer.

31. The sensor of claim 19, wherein two flow rate-determining electrodes are employed, one of said flow rate-determining electrodes being upstream of said working electrode and the other of said flow rate-determining electrodes being downstream of said working electrode.

32. A method for determining the rate of flow of a sample of fluid in a sensor having a channel, wherein said sample of fluid flows in said channel, said method comprising the steps of:
  (a) providing the sensor of claim 19;
  (b) determining responses of said working electrode and responses of said flow rate-determining electrode at known rates of flow of fluid;
  (c) establishing a relationship between said responses measured in step (b) and said rates of flow of fluid in step (b);
  (d) determining the response of said working electrode and the response of said flow rate-determining electrode at an unknown rate of flow of said sample of fluid; and
  (e) determining the value of said unknown rate of flow of said sample of fluid by means of said relationship established in step (c).

33. The method of claim 32, wherein said responses result from the formation of an electrochemically active material.

34. The method of claim 33, wherein said electrochemically active material is hydrogen peroxide.

35. The method of claim 33, wherein said electrochemically active material is oxygen.

36. A method for determining the concentration of an analyte in a sample of fluid, wherein said sample flows at an unknown rate of flow, said method comprising the steps of:
  (a) providing the sensor of claim 19;
  (b) introducing said sample of fluid to said flow channel of said sensor, said rate of flow of said sample being unknown;
  (c) determining the response of said working electrode and the response of said flow rate-determining electrode at said unknown rate of flow of said sample of fluid;
  (d) determining the value of said unknown rate of flow of said sample of fluid by means of a calibration relationship;
  (e) determining the uncorrected value of concentration of said analyte in said sample of fluid by means of a calibration relationship; and
  (f) determining the corrected value of concentration of said analyte in said sample of fluid by correcting said the uncorrected value of concentration of said analyte by means of said rate of flow determined in step (d).

37. A method for determining the rate of flow of a sample of fluid in a sensor having a channel, and the direction of flow said sample of fluid in said sensor, wherein said sample of fluid flows in said channel, said method comprising the steps of:
  (a) providing a sensor for determining the rate of flow of a fluid, said sensor comprising a channel through which said fluid flows, said channel constructed so that said fluid is capable of coming into contact with:
    (1) a working electrode;
    (2) two flow rate-determining electrodes, one of said flow rate-determining electrodes being upstream of said working electrode and the other of said flow rate-determining electrodes being downstream of said working electrode;
    (3) a reference electrode; and
    (4) a counter electrode;
  (b) determining responses of said working electrode and responses of said flow rate-determining electrodes at known rates of flow of fluid and in a first given direction of flow of fluid;
  (c) establishing a relationship between the responses measured in step (b) and the rates of flow of fluid in step (b) and the direction of flow of fluid in step (b);
  (d) determining responses of said working electrode and responses of said flow rate-determining electrodes at known rates of flow of fluid and in a second given direction of flow of fluid;
  (e) establishing a relationship between the responses measured in step (d) and the rates of flow of fluid in step (d) and the direction of flow of fluid in step (d);
  (f) determining the response of said working electrode and the response of one of said flow rate-determining electrodes at an unknown rate of flow of said sample of fluid and in an unknown direction of flow of said sample of fluid; and
  (g) determining the direction of flow of said sample of fluid and said value of said unknown rate of flow said sample of fluid by means of said relationships established in step (c) and step (e).

38. A method for determining the rate of flow of a sample of fluid in a sensor having a channel, and the direction of flow of said sample of fluid in said sensor, wherein said sample of fluid flows in said channel, said method comprising the steps of:

(a) providing a sensor for determining the rate of flow of a sample of fluid, said sensor comprising a channel through which said fluid flows, said channel constructed so that said fluid is capable of coming into contact with:

(1) a working electrode;

(2) two flow rate-determining electrodes, one of said flow rate-determining electrodes being upstream of said working electrode and the other of said flow rate-determining electrodes being downstream of said working electrode;

(3) a dual-purpose electrode that performs the functions of a reference electrode and a counter electrode;

(b) determining responses of said working electrode and responses of said flow rate-determining electrodes at known rates of flow of fluid and in a first given direction of flow of fluid;

(c) establishing a relationship between the responses measured in step (b) and the rates of flow of fluid in step (b) and the direction of flow of fluid in step (b);

(d) determining responses of said working electrode and responses of said flow rate-determining electrodes at known rates of flow of fluid and in a second given direction of flow of fluid;

(e) establishing a relationship between the responses measured in step (d) and the rates of flow of fluid in step (d) and the direction of flow of fluid in step (d);

(f) determining the response of said working electrode and the response of one of said flow rate-determining electrodes at an unknown rate of flow of said sample of fluid and in an unknown direction of flow of said sample of fluid; and (g) determining the direction of flow of said sample of fluid and said value of said unknown rate of flow of said sample of fluid by means of said relationships established in step (c) and step (e).

39. A sensor for determining the rate of flow of a fluid containing an analyte of interest, said sensor comprising a channel through which said fluid flows, said channel constructed so that said fluid is capable of coming into contact with:

(a) a flow rate-determining electrode, wherein a reaction layer overlies said flow rate-determining electrode and said reaction layer contains a reagent that reacts with the analyte of interest;

(b) a reference electrode; and (c) a counter electrode.

40. The sensor of claim 39, wherein a diffusion layer overlies said flow rate-determining electrode.

41. The sensor of claim 39, wherein a diffusion layer overlies said reaction layer.

42. The sensor of claim 41, wherein a semi-permeable layer is placed between said flow rate-determining electrode and said reaction layer.

43. A method for determining the rate of flow of a sample of fluid containing an analyte, said method comprising the steps of:

(a) providing the sensor of claim 39;

(b) determining responses of said flow rate-determining electrode at known rates of flow of samples of fluid, said samples of fluid having known concentrations of said analyte;

(c) establishing a relationship between said responses of said flow rate-determining electrode and said known rates of flow of samples of fluid having known concentrations of said analyte;

(d) determining the response of said flow rate-determining electrode where the rate of flow of fluid is unknown and the concentration of analyte in said fluid is known; and (e) determining the rate of flow of fluid from said relationship of step (c).

44. A sensor for determining the rate of flow of a fluid containing an analyte of interest, said sensor comprising a channel through which said fluid flows, said channel constructed so that said fluid is capable of coming into contact with:

(a) a flow rate-determining electrodes, wherein a reaction layer overlies said flow rate-determinina electrode and said reaction layer contains a reagent that reacts with the analyte of interest; and (b) a dual-purpose electrode that performs the functions of a reference electrode and a counter electrode.

45. The sensor of claim 44, wherein a diffusion layer overlies said flow rate-determining electrode.

46. The sensor of claim 44, wherein a diffusion layer overlies said reaction layer.

47. The sensor of claim 46, wherein a semi-permeable layer is placed between said flow rate-determining electrode and said reaction layer.

48. A method for determining the rate of flow of a sample of fluid containing an analyte, said method comprising the steps of:

(a) providing the sensor of claim 44;

(b) determining responses of said flow rate-determining electrode at known rates of flow of samples of fluid, said samples of fluid having known concentrations of said analyte;

(c) establishing a relationship between said responses of said flow rate-determining electrode and said known rates of flow of samples of fluid having known concentrations of said analyte;

(d) determining the response of said flow rate-determining electrode where the rate of flow of fluid is unknown and the concentration of analyte in said fluid is known; and (e) determining the rate of flow of fluid from said relationship of step (c).

* * * * *